(12) United States Patent
Laird et al.

(10) Patent No.: US 7,838,624 B2
(45) Date of Patent: Nov. 23, 2010

(54) MIXED HALOGEN POLYMERIZATION

(75) Inventors: Darin Laird, Pittsburgh, PA (US); Elena Sheina, Pittsburgh, PA (US)

(73) Assignee: Plextronics, Inc., Pittsburgh, PA (US)

( * ) Notice: Subject to any disclaimer, the term of this patent is extended or adjusted under 35 U.S.C. 154(b) by 63 days.

(21) Appl. No.: 12/153,180

(22) Filed: May 14, 2008

(65) Prior Publication Data

US 2009/0066233 A1 Mar. 12, 2009

Related U.S. Application Data

(60) Provisional application No. 60/938,166, filed on May 15, 2007, provisional application No. 61/043,063, filed on Apr. 7, 2008.

(51) Int. Cl.
*C08G 75/00* (2006.01)
(52) U.S. Cl. ...................................... 528/380; 528/377
(58) Field of Classification Search .................. 528/379, 528/380
See application file for complete search history.

(56) References Cited

U.S. PATENT DOCUMENTS

| 2005/0080219 A1 | 4/2005 | Koller et al. |
| 2006/0155105 A1 | 7/2006 | Werner et al. |
| 2007/0045614 A1 | 3/2007 | Sugawara et al. |

FOREIGN PATENT DOCUMENTS

| EP | 1 028 136 A2 | 8/2000 |
| EP | 1582523 A1 * | 10/2005 |
| WO | WO2005/014691 A2 | 2/2005 |
| WO | WO2006/084545 A | 8/2006 |
| WO | WO2008/028166 | 3/2008 |

OTHER PUBLICATIONS

U.S. Appl. No. 11/350,271, filed Feb. 9, 2006, Williams et al.
U.S. Appl. No. 11/376,550, filed Mar. 16, 2006, Williams et al.
U.S. Appl. No. 11/394,202, filed Mar. 31, 2006, McCullough et al.
U.S. Appl. No. 11/743,587, filed May 2, 2007, Laird et al.
U.S. Appl. No. 11/849,229, filed Aug. 31, 2007, McCullough et al.
U.S. Appl. No. 60/612,640, filed Sep. 24, 2004, Williams et al.
U.S. Appl. No. 60/612,641, filed Sep. 24, 2004, Williams et al.
U.S. Appl. No. 60/651,211, filed Feb. 10, 2005, Williams et al.
U.S. Appl. No. 60/661,934, filed Mar. 16, 2005, Williams et al.
U.S. Appl. No. 60/812,916, filed Jun. 13, 2006.
U.S. Appl. No. 60/841,548, filed Sep. 1, 2006, McCullough et al.
U.S. Appl. No. 60/915,632, filed May 2, 2007.
U.S. Appl. No. 60/938,166, filed May 15, 2007, Sheina et al.
Boymond et al., Angew. Chem. Int. Ed., vol. 37, No. 12, pp. 1701-1703 (1998).
Chen et al., " ", J. Am. Chem. Soc., vol. 117, pp. 233 (1995).
Greene and Greene, "Protective Groups in Organ Synthesis," John Wiley & Sons, New York (1981).
Iovu et al., Macromolecules, vol. 38, pp. 8649 (2005).
Lowe et al., Adv. Mater., vol. 11, pp. 250 (1999).
March, Adv. Orgn. Chem., Reactions, Mechanisms, and Science, 6th Ed., (2007).
McCullough et al., J. Org. Chem., vol. 58, pp. 904-912 (1993).
McCulough et al., Synth. Mt., vol. 67, pp. 279 (1995).
Sheina et al., Macromolecules, vol. 37, pp. 3526 (2004).
Weinshenker et al., J. Org. Chem., vol. 40, pp. 1966 (1975).
Anderson et al., "Regioselective Polymerization of 3-(4-Octylphenyl)thiophene with FeC13", Macromolecules, vol. 27, No. 22, pp. 6503-6506 (1994).
Andersson et al., "Electroluminescence from substituted poly(thiophenes): from blue to near-infrared", Macromolecules, vol. 28, pp. 7525-7529 (1995).
Andersson et al., "Synthesis of regioregular phenyl substituted polythiophenes with FeC13", Synthetic Metals, vol. 101, pp. 11-12 (1999).
Corina et al., "Experimental Evidence for the Quasi-'Living' Nature of the Grignard Metathesis Method for the Synthesis of Regioregular Poly(3-alkylthiophenes)", Macromolecules, vol. 38, pp. 8649-8656 (2005).
Goto et al., "Solvent-induced chiroptical changes in supramolecular assemblies of an optically active, regioregular polythiophene", Macromolecules, vol. 35, pp. 4590-4601 (2002).
Jeffries-El et al., "Facile Synthesis of End-Functionalized Regioregular Poly(3-alkylthiophene)s via Modified Grignard Metathesis Reaction", Macromolecules, vol. 38, pp. 10346-10352 (2005).
Johansson et al., "Light-emitting electrochemical cells from oligo(thylene oxide)-substituted polythiophenes: evidence for in situ doping", Chem. Mater., vol. 11, pp. 3133-3139 (1999).
Loewe et al., "Regioregular, head-to-tail coupled poly(3-alkylthiphenes) made easily by the GRIM method: investigation of the reaction and the origin of the regioselectivity", Macromolecules, vol. 34, pp. 4324-4333 (2001).
Mellah et al., "Electroreductive polymerization of 3-substituted 2,5-dihalothiophenes: direct electrosynthesis versus stepwise procedure involving thienylzinc intermediates", New. J. Chem., vol. 26, pp. 207-212 (2002).
Tyo et al., "Synthesis of unsymmetrical 2, 3-diaryl-and 2,4-diarylthiophenes starting from 2,5-dichlorothiophene", Bulletin of the Chem. Soc. of Japan, vol. 67, No. 8, pp. 2187-2194 (1994).
Yokoyama et al., "Chain-growth polymerization for poly(3-hexylthiophene) with a defined molecular weight and a low polydispersity", Macromolecules, vol. 37, pp. 1169-1171 (2004).
Zhai et al., "A simple method to generate side-chain derivatives of regioregular polythiophene via the GRIM metathesis and post-polymerization functionalization", Macromolecules, vol. 36, pp. 61-64 (2003).
PCT/US2008/006117 filed May 14, 2008, Intl. Search Report & Written Opinion mailed Jan. 13, 2009 (21 pages).

* cited by examiner

*Primary Examiner*—Randy Gulakowski
*Assistant Examiner*—Shane Fang
(74) *Attorney, Agent, or Firm*—Foley & Lardner LLP

(57) ABSTRACT

Synthesis of regioregular thiophene-based polymers (PTs) and their functionalized counterparts via metal assisted cross-coupling polymerizations utilizing mixed halogen substituted aryl halide monomer precursors. The described method provides a means to control structural homogeneity and regioregularity and the electronic/spectroscopic properties of functionalized PTs, and leads to improved performance of organic semiconductor devices such as OPVs and/or OFETs. Asymmetrical monomers can be used.

16 Claims, No Drawings

MIXED HALOGEN POLYMERIZATION

RELATED APPLICATIONS

This application claims priority to U.S. provisional applications 60/938,166 filed May 15, 2007 and 61/043,063 filed Apr. 7, 2008, the two complete disclosures of which are hereby incorporated by reference in their entireties.

BACKGROUND

Organic materials provide exciting prospects for applications in electronic devices including, for example, printed electronics, solar cells, light-emitting diodes, and thin film transistors. In particular, solar cells (or photovoltaic devices (PVs)) are important due to a growing economic need for a practical source of renewable energy that will substantially reduce dependence upon fossil fuels. Silicon-based solar energy systems have been touted for years as potential candidates. However, the capital-intensive nature of silicon manufacturing processes contributes to a cost structure that falls significantly short of commercial viability. Photovoltaic cells, or solar cells, based on Inherently Conductive (or generally used, Conducting) Polymers (ICPs) (such as polyacetylene, polythiophene, polyaniline, polypyrrole, polyfluorene, polyphenylene, polycarbazole, and poly(phenylene vinylene) offer a great potential as significantly lower-cost devices because these polymers can be handled like inks in conventional printing processes.

Alternative sources of energy, especially renewable energy, are being sought to dramatically change the functional and cost boundaries resulting from current energy sources. This need is heightened by the rapidly increasing cost, environmental impact, and geo-political implications of the world's reliance on fossil fuels. Regulations from the global level (e.g., Kyoto Treaty) to the local level increase the demand for cost-effective renewable energy supply. The use of the sun's rays to create power represents an attractive, zero-emission source of renewable energy.

Conjugated polymers are a key component of a new generation of organic solar cells (or organic photovoltaics (OPVs)) that promises to significantly reduce the cost/performance barrier of existing inorganic counterparts. The primary advantage of an organic solar cell is that the core materials, and the device itself, present flexible, light-weight design advantages and can be manufactured on an industrial scale in a low-cost manner. Organic components can be solution processed and printed by standard printing techniques to form thin films. However, while this technology holds great promise, commercialization hurdles remain. There is a great demand for materials with a fine balance of processability, stability, electronic and spectroscopic properties (e.g., conductivity, charge transport, band gap, energy spacing between the HOMO and LUMO levels (highest occupied and lowest unoccupied molecular orbitals, respectively) that would substantially improve OPV performance.

Among the multitude of conducting polymers investigated to date, polythiophene (PT) and its derivatives continue to represent a versatile conjugated polymer system. This is largely due to their exceptional spectroscopic and electronic properties, potential ease of processing, relative robustness, and light weight. In order to influence the material properties in a desired fashion, it is of key importance to structurally control the molecular organization and molecular composition of the conjugated polymers. Extensive studies have been done with the poly(3-alkylsubstituted thiophene) (PAT) system. The initial synthetic approaches for making PATs had virtually no control over their absolute structures. Due to the presence of configurational isomers, the polymers possessed various degrees of regioregularity. The synthetic methodologies that afford regioselective synthesis of PATs are based on transition metal promoted cross-coupling reaction of organometallic compounds and halide derivatives of β-functionalized thiophenes. The scope of this type of metal-assisted cross coupling polymerizations has been expanded enormously by the development of efficient initiators or catalysts. For example, the degree of regioregularity has been shown to be controlled and affected by the ligands' influence on the metal center and the choice of the metal (Chen et al., *J. Am. Chem. Soc.* 1995, 117, 233). Both nickel and palladium metal complexes with tailored phosphine ligands have been applied.

For the alkyl-substituted polythiophenes (e.g., poly(3-hexylthiophene) [P3HT]), with certain specifications, reaction requirements and conditions, the Grignard Metatheses (GRIM) and McCullough methodologies for the dibromofunctionalized starting monomers afford regioregular polymer. However, if the reaction conditions are altered or other thiophene derivatives (e.g., aryl-substituted thiophenes and their functionalized counterparts) are used, the regioregularity of the final polymer may not be easily controlled, despite attempted adherence to the classic GRIM and McCullough protocols. Therefore, there is a need for an improved method to achieve, for example, reproducible and structurally pure poly(3-aryl substituted thiophene) products. Furthermore, for scaling up processes for PATs (including P3HT) it becomes of a challenge to control regioregularity with some methodologies (e.g., the GRIM method applied for the industrial production of P3HT). As a result, a better methodology is needed.

SUMMARY

Embodiments described herein include compositions, devices, methods of making compositions and devices, and methods of using compositions and devices.

For example, one embodiment provides a method of making poly(3-arylsubstituted) thiophene, comprising: providing at least one monomer represented by:

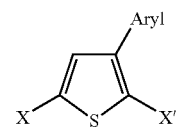

wherein X is I and X' is Br, or X is I and X' is Cl, or X is Br and X' is Cl; and polymerizing the monomer. The aryl substituent is not particularly limited and adapted to allow polymerization of the monomer.

Another embodiment provides a method comprising: providing an unsaturated ring compound comprising at least two halogen ring substituents, wherein a first halogen ring substituent is iodo and a second halogen ring substituent is bromo; providing an organomagnesium reagent comprising an organomagnesium component and a metal activation agent; combining the unsaturated ring compound with the reagent to form a second compound by metal-halogen exchange, wherein the metal activation agent activates the metal halogen exchange; and exposing the second compound to at least one transition metal initiator to produce an oligomerization or polymerization reaction.

Another embodiment provides a method comprising: providing at least one asymmetrical organic dihalogen polymerization monomer adapted for metal-assisted cross coupling polymerization, wherein the monomer comprises at least one thiophene ring which is substituted with an aryl group, and wherein the monomer comprises an X halogen group and an X' halogen group, wherein X and X' are different and independently Cl, Br, or I, and polymerizing the monomer.

Another embodiment provides a composition comprising: at least one thiophene compound comprising an aryl substituent at the 3-position, a first halogen substituent at the 2-position, and a second halogen at the 5-position, wherein the first and second halogens are different halogens.

One or more embodiments described herein can lead to significantly improved performance in organic electronic devices. The polymers produced as described herein can be used in active layer technology for printed organic electronics—polymer solar cells (or organic photovoltaics (OPVs)), light emitting diodes, sensor devices, plastic circuitry (e.g., organic field effect transistors (OFETs)), and other electronic devices that utilize semiconducting conjugated polymers. For example, efficiency in an OPV can be improved. In addition, mobility and ION values can be improved for OFETs.

DETAILED DESCRIPTION

Introduction

All references cited herein are incorporated by referenced in their entireties.

U.S. Provisional Patent Application 60/938,166 filed May 15, 2007 to Sheina et al., describes polymer products, compositions, devices, and articles, some of which prepared by using the embodiments of the present invention. This application is herein incorporated by reference in its entirety including the description, the figures, and the claims.

U.S. Pat. No. 6,166,172 describes the GRIM method of forming a regioregular poly (3-substitutedthiophene) from a polymerization reaction. The method proceeds by combining a soluble thiophene having at least two leaving groups with an organomagnesium reagent to form a regiochemical isomer intermediate, and adding thereto an effective amount of, for example, Ni(II) complex to initiate the polymerization reaction.

Provisional patent application Ser. No. 60/612,640 filed Sep. 24, 2004, to Williams, et al. ("HETEROATOMIC REGIOREGULAR POLY(3-SUBSTITUTED THIOPHENES) FOR ELECTROLUMINESCENT DEVICES"), and U.S. Ser. No. 11/234,374 filed Sep. 26, 2005, are hereby incorporated by reference in their entirety, including the description of the polymers, the figures, and the claims.

Provisional patent application Ser. No. 60/612,641 filed Sep. 24, 2004, to Williams, et al. ("HETEROATOMIC REGIOREGULAR POLY (3-SUBSTITUTED THIOPHENES) FOR PHOTOVOLTAIC CELLS"), and U.S. Ser. No. 11/234,373 filed Sep. 26, 2005, are hereby incorporated by reference in their entirety, including the description of the polymers, the figures, and the claims.

Provisional patent application Ser. No. 60/651,211 filed Feb. 10, 2005, to Williams, et al. ("HOLE INJECTION LAYER COMPOSITIONS"), and U.S. Ser. No. 11/350,271 filed Feb. 9, 2006, are hereby incorporated by reference in their entirety, including the description of the polymers, the figures, and the claims.

Priority provisional patent application Ser. No. 60/661,934 filed Mar. 16, 2005, to Williams, et al., and U.S. Ser. No. 11/376/550 filed Mar. 16, 2006, are hereby incorporated by reference in their entirety, including the description of the polymers, the figures, and the claims.

Provisional patent application Ser. No. 60/812,916 filed Jun. 13, 2006 ("ORGANIC PHOTOVOLTAIC DEVICES COMPRISING FULLERENES AND DERIVATIVES THEREOF"), and U.S. patent application Ser. No. 11/743,587 filed May 2, 2007, are hereby incorporated by reference in their entirety, including the descriptions of the polymers, the n-components including indene derivatives, the figures and the claims.

Provisional patent application Ser. No. 60/915,632 filed May 2, 2007 ("SOLVENT BLENDS IN ACTIVE LAYER CONDUCTING POLYMER TECHNOLOGY FOR PRINTED ELECTRONIC DEVICES") is hereby incorporated in its entirety, including the description of the polymers, the solvent blends, the figures and the claims.

Additional description of methods, compositions, and polymers can be found in, for example, McCullough et al., *J. Org. Chem.*, 1993, 58, 904-912, and U.S. Pat. No. 6,602,974 to McCullough, et al.

Additional description can be found in the articles, "The Chemistry of Conducting Polythiophenes," by Richard D. McCullough, *Adv. Mater.*, 10, No. 2, 93-116, and references cited therein, and Lowe, et al., *Adv. Mater.* 1999, 11, 250, which are hereby incorporated by reference in its entirety. The *Handbook of Conducting Polymers,* 2nd Ed., 1998, Chapter 9, by McCullough, et al., "Regioregular, Head-to-Tail Coupled Poly(3-alkylthiophene) and its Derivatives," pages 225-258, is also hereby incorporated by reference in its entirety.

Grignard metathesis reactions are known in the art, an example of which is described by L. Boymond et al., *Angew. Chem. Int. Ed.*, 1998, 37, No. 12, pages 1701-1703, which is incorporated herein by reference in its entirety. If a side group R on a monomer is reactive with the organomagnesium reagent, a protective group can be coupled with the R-group to prevent the R-group from taking part in the synthesis. The use of protective groups with a reactive R-group is well known in the art, as described by Greene and Greene, "*Protective Groups in Organic Synthesis,*" John Wiley and Sons, New York (1981), which is incorporated herein by reference. One skilled in the art can use protective groups and deprotection synthetic strategies in order to introduce certain functional groups which may otherwise be undesirably reactive under certain desired reaction conditions. See, for example, March's *Advanced Organic Chemistry, Reactions, Mechanisms, and Structure, 6$^{th}$ Ed,* 2007.

"Optionally substituted" groups refers to functional groups that may be substituted or unsubstituted by additional functional groups. When a group is unsubstituted by an additional group it may be referred to as a group name, for example alkyl or aryl. When a group is substituted with additional functional groups it may more generically be referred to as substituted alkyl or substituted aryl, respectively.

"Aryl" refers to an aromatic carbocyclic group of from 6 to 20 carbon atoms having a single ring (e.g., phenyl) or multiple condensed rings (e.g., naphthyl or anthryl) which condensed rings may or may not be aromatic provided that the point of attachment is at an aromatic carbon atom. Preferred aryls include phenyl, naphthyl, and the like.

"Alkyl" refers to straight chain and branched alkyl groups having from 1 to 20 carbon atoms, or from 1 to 15 carbon atoms, or from 1 to 10, or from 1 to 5, or from 1 to 3 carbon atoms. This term is exemplified by groups such as methyl, ethyl, n-propyl, iso-propyl, n-butyl, t-butyl, n-pentyl, ethylhexyl, dodecyl, isopentyl, and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propyloxy, iso-propyloxy, n-butyloxy, t-butyloxy, n-pentyloxy, 1-ethylhex-1-yloxy, dodecyloxy, isopentyloxy, and the like, and also includes alkoxyalkoxy moieties such as for example methoxyethoxy or methoxyethoxyethoxy.

"Substituted alkoxy" refers to the group "substituted alkyl-O—."

"Alkenyl" refers to alkenyl group preferably having from 2 to 6 carbon atoms and more preferably 2 to 4 carbon atoms and having at least 1 and preferably from 1-2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Aryloxy" refers to the group aryl-O— that includes, by way of example, phenoxy, naphthoxy, and the like.

"Alkynyl" refers to alkynyl group preferably having from 2 to 6 carbon atoms and more preferably 2 to 3 carbon atoms and having at least 1 and preferably from 1-2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Conjugated polymer" refers to chemical compounds comprising repeating structural units, or monomers, connected by covalent chemical bonds and have points of conjugated unsaturation. Conjugated unsaturation refers to a system of atoms covalently bonded with alternating single and multiple bonds. The system results in a general delocalization of the electrons across all of the adjacent parallel aligned p-orbitals of the atoms. The number of repeating units in a polymer is generally more than two, and typically more than five or even more typically more than ten.

"A polythiophene" or "polythiophene" refers to polymers comprising a thiophene in the backbone including polythiophene, derivatives thereof, and copolymers and terpolymers thereof.

"Regioregular polythiophene" refers to polythiophene having high levels of regioregularity including for example at least 80%, or at least 90%, or at least 95%, or at least 98%, or at least 99%.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Other terms used herein are defined as follows, unless the context makes clear otherwise.

Monomer for Poly(3-Arylsubstituted)Thiophene

Although the presently claimed inventions are not necessarily limited by theory, embodiments described herein can benefit by different bond strengths of halogen bonded to the ring to facilitate selective reactivity.

Asymmetrical monomers can be polymerized include monomers comprising at least one thiophene ring.

In some embodiments, a 2,5-mixed halogen substituted thiophene monomer is provided which can be represented by:

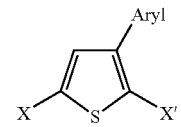

wherein X and X' are different and can be Cl, Br, or I. In one embodiment, X is I and X' is Br, and in another embodiment, X is I and X' is Cl, and in another embodiment, X is Br and X' is Cl.

The aryl group is not particularly limited as long as it is adapted to allow for polymerization of the monomer. It can comprise, for example, one, two, or three, or more optionally substituted phenyl groups. The aryl group can comprise at least one chiral substituent.

In some embodiments, the thiophene monomer is substituted at 3-position by an aryl which can be substituted independently with for example H, optionally substituted $C_1$-$C_{20}$ linear or branched alkyl, alkenyl, alkynyl, or alkoxyl.

In particular, the aryl group can be an optionally substituted phenyl group. More particularly, the aryl group can be a substituted phenyl group comprising a branched alkyl substituent. For example, the aryl group can be a 4-(2-ethylhexyl) phenyl group.

Polymerization of the Monomer

The monomer can be polymerized by methods known in the art. For example, the polymerization step can comprise (i) reacting the monomer with an organomagnesium reagent to form an intermediate, and (ii) reacting the intermediate with at least one metal complex. As described further below, the organomagnesium reagent can comprise an organomagnesium component and a metal activation agent. In addition to an organomagnesium reagent, other reagents such as zinc reagents including organozinc reagents can be used if desired.

The polymerizing step can comprise, for example, dissolving the monomer in at least one solvent to form a mixture, adding at least one organomagnesium reagent to the mixture, adding an initiator to the mixture, and recovering a poly(3-arylsubstituted thiophene).

For example, monomer can be reacted with an organomagnesium reagent such as isopropylmagnesium chloride in the presence of a solvent for a period of time. A metal complex such as for example a polymerization Ni (II) initiator can be added and the reaction proceeds for a period of time sufficient to produce the desired yield of regioregular polythiophene.

In one embodiment, polymerization can be carried out under living or substantially living conditions. See, for example, U.S. patent application Ser. No. 11/394,202 filed Mar. 31, 2006 to McCullough et al., which is hereby incorporated by reference in its entirety.

The polymerizing step can produce an oligomer, a polymer, or a copolymer, including a terpolymer and block copolymers.

In some embodiment, the polymer product comprises a fragment of the following formula, wherein the end groups may or may not be known:

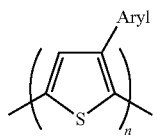

Copolymerization can be carried out including formation of random copolymers.

Copolymers Including Block Copolymers

Polymerizing or copolymerizing can be carried out in the presence of a polymer with active end group so that a block copolymer forms. The end groups are not particularly limited so long as a block copolymer can be formed. For example, the polymer with active end group can be a polythiophene including a regioregular polythiophene. More particularly, the polymer with active end groups can be a thiophene-based polymer comprising alkyl, alkoxy, aryl, or a combination thereof side groups. In particular, the polythiophene can be for example a poly(3-alkylthiophene).

In one embodiment, the block copolymer can be an A-B or an A-B-A or an A-B-C type block copolymer. The A, B, and C blocks can be, for example, all polythiophene blocks. For example, one block can be an alkyl-substituted polythiophene block, whereas another block can be an aryl-substituted polythiophene block.

In one embodiment, the block copolymer can be represented by following structure:

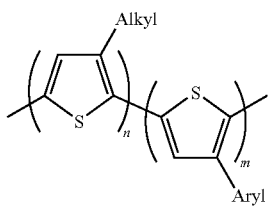

wherein n can be 1 to about 500, and m can be about 1 to about 500, and the alkyl group can be for example C1 to C20, or more particularly, C5 to C12. Alternatively, n can be 1 to about 300, and m can be about 1 to about 300, and the alkyl group can be for example C1 to C20, or more particularly, C5 to C12.

Asymmetrical Monomers

A variety of additional types of asymmetrical monomers can be polymerized by methods described herein using the mixed halogen approach. The monomer can comprise two or more heterocyclic rings including two or more thiophene rings. For example, the monomer can be an asymmetrical monomer represented by:

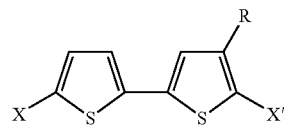

wherein X is I and X' is Br, or X is I and X' is Cl, or X is Br and X' is Cl, and R is a substituent adapted to allow for polymerization of the monomer; or

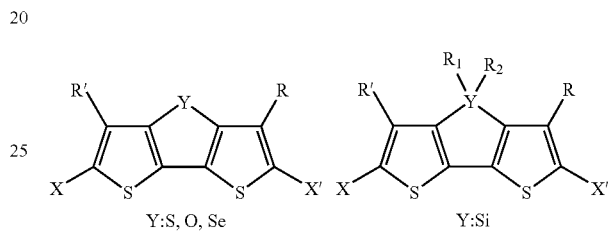

Y:S, O, Se          Y:Si wherein X is I and X' is Br, or X is I and X' is Cl, or X is Br and X' is Cl, and R, R', $R_1$, and $R_2$ are substituents adapted to allow for polymerization of the monomer; or

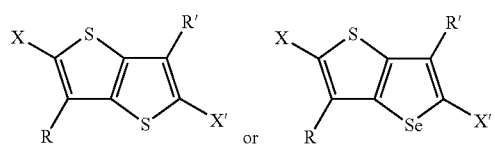

wherein X is I and X' is Br, or X is I and X' is Cl, or X is Br and X' is Cl, and R and R' are substituents adapted to allow for polymerization of the monomer.

Examples of the substituents R, R', $R_1$, and $R_2$ are not particularly limited if they are compatible with polymerization and provide an asymmetrical monomer. Examples include optionally substituted alkyl, optionally substituted aryls, and substituents with heteroatomic atoms such as oxygen including for example optionally substituted alkoxy substituents.

Universal Grim

In addition, U.S. Provisional Patent Application No. 60/841,548, filed on Sep. 1, 2006 to McCullough et al, and U.S. Regular patent application Ser. No. 11/849,229, filed on Aug. 31, 2007 to McCullough et al., its corresponding PCT/US2007/077461 published as WO2008/028166, describe the Universal GRIM method. Asymmetrical monomers can be polymerized by this approach. This application, in one embodiment, provides for a method comprising: providing an unsaturated ring compound comprising at least two halogen ring substituents, providing an organomagnesium reagent comprising an organomagnesium component and a metal activation agent, combining the unsaturated ring compound with the reagent to form a second compound by metal-halogen exchange, wherein the metal activation agent activates the metal-halogen exchange, and coupling the second compound in an oligomerization or polymerization reaction.

Presently, a first halogen ring substituent can be, for example, a 5-iodo and a second halogen ring substituent can be 2-bromo; or the first halogen ring substituent can be a 5-iodo and a second halogen ring substituent can be 2-chloro; or the first halogen ring substituent can be a 5-bromo and a second halogen ring substituent can be 2-chloro.

In some embodiments, a regioregular poly (3-substituted thiophene) can be prepared via the modified or universal GRIM method. In these embodiments, a 2,5-mixed halogen substituted thiophene monomer of formula III can be used:

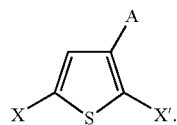

(Formula III)

For example, the monomer in formula III can be substituted at the 3-position by a group A which can be any group adapted to allow polymerization of the monomer. For example, the A group can be an optionally substituted linear or branched alkyl group or an optionally substituted aryl group. The aryl group may be an optionally substituted aromatic or heteroaromatic group, the optional substituent can be independently H, $C_1$-$C_{20}$ linear and branched alkyl, alkenyl, akynyl, alkoxyl, alkoxyalkyl.

The monomer of Formula III can be reacted with an organomagnesium reagent such as isopropylmagnesium chloride in presence of a metal salt, such as $ZnCl_2$ and LiCl, and a suitable solvent for a period of time. A polymerization Ni (II) initiator or catalyst can be added and the reaction proceeds for a period of time sufficient to produce the desired yield of regioregular polythiophene derivatives. X and X' are different and may be Cl, Br, or I. More specifically X and X' can be, for example, I and Br respectively, or I and Cl, respectively, or Br and Cl respectively.

In some embodiments, the polymer product comprises a fragment of the following formula:

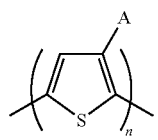

The group A can be any group adapted to allow polymerization of the monomer In some embodiments, the A group can be an aryl group which can be an optionally substituted phenyl group. More specifically, the aryl can be for example 4-(2-ethylhexyl)phenyl group. A homopolymer as well as a copolymer can be prepared via these methods.

Block copolymers can be made. In some embodiments, the copolymer is of the following formula:

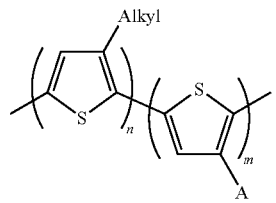

Wherein in this Formula, n and m represent the degree of polymerization. The groups Alkyl and A can be groups as described herein.

In making the copolymer above, the method can further comprise a step of adding a 3-alkylsubstituted thiophene monomer to an existing polymer in a block copolymerization, wherein the monomer can be represented by:

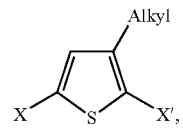

wherein X and X' may be Cl, Br, or I, and in particular X can be I and X' can be Br, or X can be I and X' can be Cl, or X can be Br and X' can be Cl.

The present invention also provides for polymers produced according to the methods of the present invention, a composition and device comprising the polymers produced according to the present invention.

In some embodiments, the polymer product comprises a fragment of the following formula:

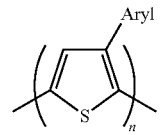

Wherein Aryl can be a groups as described herein.

The polymer may be homopolymer or copolymer. It may be a block or a random copolymer. In some other embodiments, the present invention provides for a copolymer of the following structure:

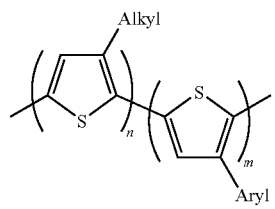

In some embodiments, the polymer product comprises a fragment of the following formula:

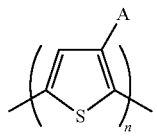

The polymer may be copolymer or homopolymer. The polymer may be a random or a block copolymer. In some embodiments, the copolymer is of the following formula:

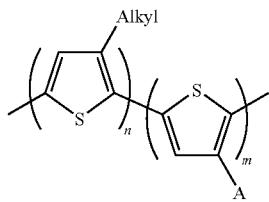

where n and m represent the degree of polymerization.

Another embodiment using approaches described in the McCullough '229 application provides for a method comprising: providing a heterocyclic, aromatic, or biphenyl ring compound comprising at least two halogen ring substituents which are different such as for example I and Br, providing an organomagnesium reagent comprising an organomagnesium component and a lithium activation agent, combining the ring compound with the organomagnesium reagent to form a second compound, polymerizing the second compound with transition metal complex to form a conjugated polymer.

Another embodiment making use of the McCullough '229 application provides a method comprising: providing a heterocyclic, aromatic, or biphenyl ring compound comprising two halogen ring substituents, including for example an I substituent and a Br substituent, providing a magnesium are complex, combining the ring compound with the complex to form a second compound, polymerizing the second compound with transition metal complex to form a conjugated polymer.

One or more advantages which can be found in one or more embodiments described in the McCullough '229 application include high yields, fast reaction speeds, simple conditions, commercially available reagents, generally commercially attractive polymerization conditions, an expansion of the commercially attractive GRIM method to new and commercially important polymers, and new routes to blue light emitters.

Characterization of Polymers

The polymer produced according to the methods described herein can be regioregular or comprise regioregular segments or fragment(s). In some embodiments, the regioregularity is at least 50%. In some embodiments, the regioregularity is at least 75%. In some embodiments, the regularity is at least 90% or at least 95% or at least 98%.

Molecular weight is not particularly limited. For example, Mn can be for example about 1,000 to about 1,000,000, or about 2,000 to about 100,000, or about 3,000 to about 75,000.

The present invention provides for a composition and a device comprising a polymer as described herein. Devices can be fabricated including for example OLED, solar cell or OPV, and transistor (OFET) devices.

A series of non-limiting working examples are provided.

WORKING EXAMPLES

Working Example 1

Synthesis of Monomers Used to Produce Aryl-substituted Polythiophenes

This Example describes the methods used to produce the monomer reactants used to produce the aryl-substituted polythiophenes, as described in Examples 2-8.

Example 1a Synthesis of (2-ethylhexyl)-benzene

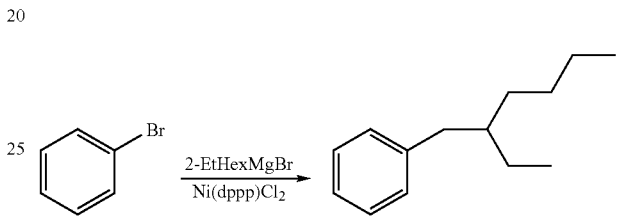

A dry 250-mL three-neck round bottom flask, equipped with a condenser and an addition funnel, was purged with $N_2$ and charged with bromobenzene (15 g, 0.10 mol), [1,3-bis (diphenylphosphino)propane]dichloronickel(II) (Ni(dppp) $Cl_2$) (0.27 g, 0.50 mol %). The reaction flask was cooled down to 0° C., whereupon (ethylhexyl)magnesium bromide 1 M solution in diethyl ether (100 mL) was added dropwise from the addition funnel over a 30-minute time period. The reaction was slightly exothermic, and a dark-brown color developed within minutes. The ice bath was replaced with an oil bath, and the solution was heated up to gentle reflux and maintained at that temperature for 12 hours, then cooled in an ice bath, and quenched with cold HCl (100 mL, 1.0 N). The aqueous layer was separated and extracted with diethyl ether (3×100 mL). The combined organic phase was collected and dried over anhydrous magnesium sulfate ($MgSO_4$). After the product was filtered, the solvent was removed by rotary evaporation. The crude product was distilled under vacuum to yield 3.3 g (70%) of colorless oil.

Spectral data: $^1$H NMR (300 MHz, $CDCl_3$): $\delta_H$ 0.85 (t, J=6 Hz, 6H), 1.25 (m, 8H), 1.55 (m, 1H), 2.51 (d, J=7 Hz, 2H), 7.12 (m, 5H).

Example 1b

Synthesis of 1-bromo-4-(2-ethylhexyl)-benzene

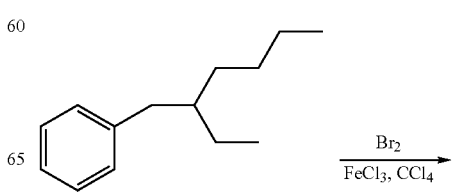

-continued

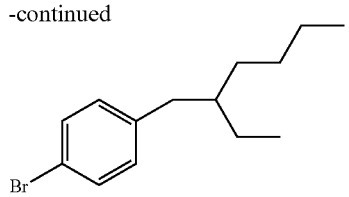

The procedure was adapted from Weinshenker, N. M. et al., *J. Org. Chem.* 1975, 40, 1966. A 100-mL round bottom flask was charged with (2-ethylhexyl)-benzene (12 g, 0.063 mol), carbon tetrachloride (20 mL), and anhydrous ferric chloride (0.10 g). A 3.9 mL solution of bromine (0.076 mol) in 10 mL of carbon tetrachloride was added. The resultant mixture was exothermic and proceeded with evolution of hydrogen bromide gas (and some bromine gas) that was neutralized with sodium hydroxide. The reaction was completed as the evolution of hydrogen bromide was finished. The solution was stirred at ambient temperature for an additional hour. After addition of aqueous sodium hydroxide (10%), the mixture was extracted with diethyl ether (3×100 mL). The combined organic layer was washed with aqueous sodium hydroxide (10%) until no yellow/brown color in the aqueous phase was observed. The organic phase was dried over anhydrous magnesium sulfate ($MgSO_4$). After the product was filtered, the solvent was removed by rotary evaporation. The crude product was distilled under vacuum to yield 13.8 g (81%) of colorless oil.

Spectral data: $^1$H NMR (300 MHz, $CDCl_3$): $\delta_H$ 0.96 (t, J=6 Hz, 6H), 1.29 (m, 8H), 1.86 (m, 1H), 2.51 (d, J=6 Hz, 2H), 7.01 (d, J=9 Hz, 2H), 7.38 (d, J=9 Hz, 2H).

Example 1c

Synthesis of 3-[4-(2-ethylhexyl)-phenyl]-thiophene

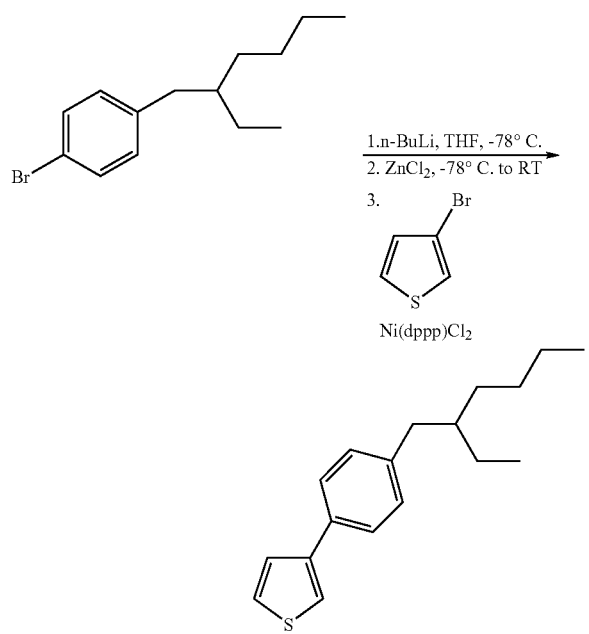

A dry 250-mL three-neck round bottom flask, equipped with a condenser, was charged with 1-bromo-4-(2-ethylhexyl)-benzene (8 g, 0.03 mol) and purged with $N_2$ followed by addition of anhydrous THF (50 mL) via a deoxygenated syringe. The reaction flask was cooled to −78° C. and n-butyllithium, a 2.5 M solution in hexane (12 mL, 0.03 mol), was added dropwise via syringe. The reaction mixture was stirred for 1 hour at −78° C. Anhydrous $ZnCl_2$ (4.09 g, 0.03 mol) was added in one portion and completely dissolved after 30 minutes of stirring. The cooling bath was removed and the reaction mixture was allowed to warm to ambient temperature, whereupon 3-bromothiophene (5.38 g, 0.03 mol) and Ni(dppp)$Cl_2$ (0.32 g, 2 mol %) were added. The solution was heated up to reflux and maintained at that temperature for 12 hours, then cooled to ambient temperature, and quenched with cold HCl (10 mL, 1.0 N). The aqueous layer was separated and extracted with diethyl ether (3×100 mL). The organic phase was collected and dried over anhydrous magnesium sulfate ($MgSO_4$). After the product was filtered, the solvent was removed by rotary evaporation. The crude product was purified by recrystallization from methanol affording 5.3 g (65%) of white solid.

Spectral data: $^1$H NMR (300 MHz, $CDCl_3$): $\delta_H$ 10.87 (t, J=6 Hz, 6H), 1.27 (m, 8H), 1.56 (m, 1H), 2.53 (d, J=8.1 Hz, 2H), 7.15 (d, J=9 Hz, 2H), 7.37 (m, 3H), 7.48 (d, J=9 Hz, 2H).

Example 1d

Synthesis of 2-bromo-3-[4-(2-ethylhexyl)-phenyl]-thiophene

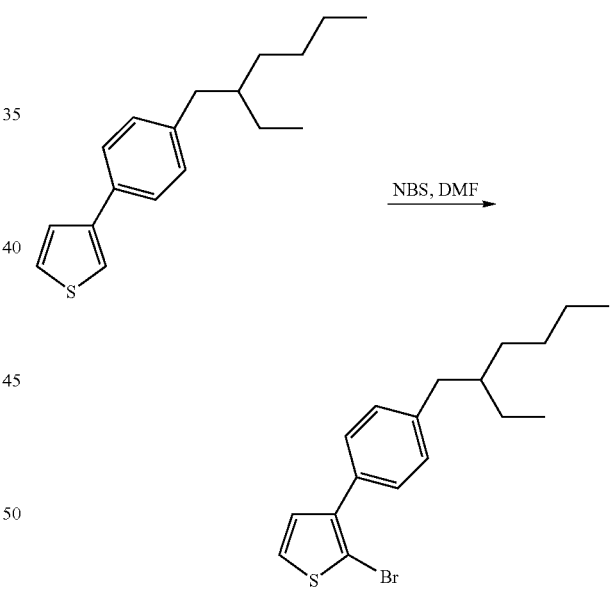

A 250-mL round bottom flask was charged with 3-[4-(2-ethylhexyl)-phenyl]-thiophene (7 g, 0.026 mol), N,N-dimethyl formamide (DMF) (65 mL). The reaction mixture was stirred at ambient temperature for 5 minutes, whereupon a 0.4 M solution of NBS (0.026 mol) in DMF was added and the stirring continued for 2 hours. After addition of water, the mixture was extracted with diethyl ether (3×150 mL). The combined organic layer was dried over anhydrous magnesium sulfate ($MgSO_4$). After the product was filtered, the solvent was removed by rotary evaporation. The crude product was purified using column chromatography on silica gel with hexane as the eluent ($R_f$=0.35). The compound was dried under vacuum to yield 8.7 g (95%) of slightly yellow oil.

Spectral data: $^1$H NMR (300 MHz, CDCl$_3$): $\delta_H$ 0.87 (t, J=6 Hz, 6H), 1.27 (m, 8H), 1.58 (m, 1H), 2.55 (d, J=7.5 Hz, 2H), 7.02 (d, J=6 Hz, 1H), 7.19 (d, J=9 Hz, 2H), 7.27 (d, J=6 Hz, 1H), 7.45 (d, J=9 Hz, 2H).

Example 1e

Synthesis of 2-bromo-3-[4-(2-ethylhexyl)-phenyl]-5-iodothiophene

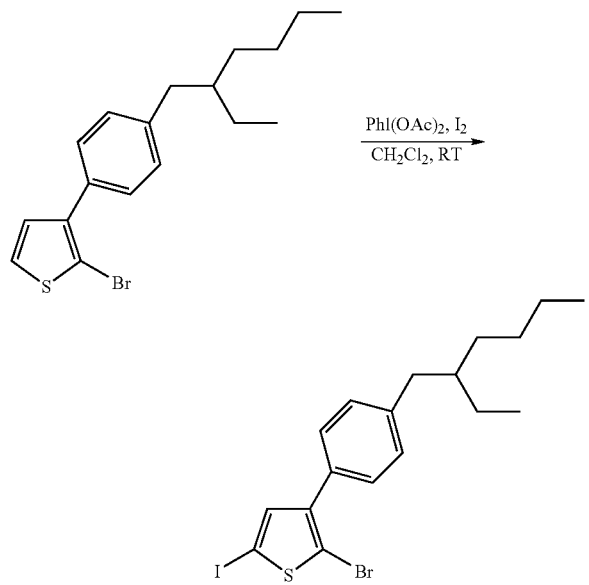

The procedure was adapted from Yokoyama, A. *Macromolecules* 2004, 37, 1169. A 100-mL round bottom flask was charged with 2-bromo-3-[4-(2-ethylhexyl)-phenyl]-thiophene (2.6 g, 7.4 mmol), purged with N$_2$, and anhydrous dichloromethane (18 mL) was added via a deoxygenated syringe. The reaction flask was cooled down to 0° C., whereupon iodine (I$_2$) (1.04 g, 4.1 mmol) and iodobenzene diacetate (PhI(OAc)$_2$) (1.4 g, 4.4 mmol) were added in one portion, and the mixture was stirred at ambient temperature for 4 hours. An aqueous solution of sodium thiosulfate (NaS$_2$O$_3$) (10%) was added to the reaction mixture; the aqueous layer was separated and extracted with diethyl ether (3×50 mL). The collected organic phase was washed with aqueous NaS$_2$O$_3$ (10%) and dried over anhydrous MgSO$_4$. After filtration, the solvent and iodobenzene were removed by evaporation under reduced pressure. The crude product was purified using column chromatography on silica gel with hexane as the eluent (R$_f$=0.38). The compound was dried under vacuum to yield 3.35 g (95%) of slightly yellow oil.

Spectral data: $^1$H NMR (300 MHz, CDCl$_3$): $\delta_H$ 0.87 (t, J=6 Hz, 6H), 1.28 (m, 8H), 1.6 (m, 1H), 2.6 (d, J=7.5 Hz, 2H), 7.19 (d, J=9 Hz, 2H), 7.18 (s, 1H), 7.39 (d, J=9 Hz, 2H).

Example 2

General Method for Making a Homopolymer (GRIM Method)

General procedure for preparation of phenyl-substituted polythiophenes via the GRIM method utilizing 2-bromo-3-[phenyl-substituted]-5-iodothiophene:

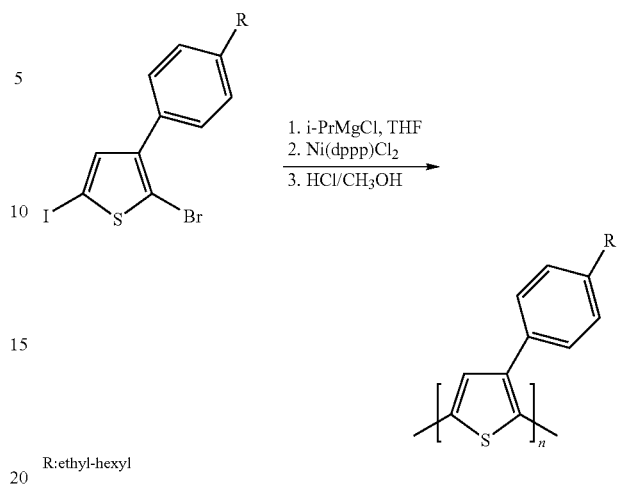

where R is a branched alkyl group, e.g. 2-ethylhexyl.

In a typical polymerization experiment, a dry 100-mL three-neck flask was charged with 2-bromo-3-[4-(2-ethylhexyl)phenyl]-5-iodothiophene (0.5 g, 1 mmol) and flushed with N$_2$, and THF (10 mL) was added via syringe. A 2-M solution of iso-propylmagnesium chloride (0.5 mL, 1 mmol) in THF was added via a deoxygenated syringe and the reaction mixture was stirred at ambient temperature for 10 minutes. A suspension of Ni(dppp)Cl$_2$ (2 mg, 0.003 mmol) in THF (0.003 M) was added via syringe. The reaction mixture was heated to 55° C. and stirred for 2 hours. Hydrochloric acid (5 N) was added and the reaction mixture was precipitated into methanol. The polymer was filtered, washed in sequence with more methanol and hexanes, and dried under vacuum. The molecular weight of the polymer was measured by GPC.

Working Example 3

Polymerization Via the Modified GRIM Method

The following polymer, poly(3-[4-(2-ethylhexyl)-phenyl] thiophene), was prepared via the modified GRIM method utilizing 2-bromo-3-[4-(2-ethylhexyl)phenyl]-5-iodothiophene:

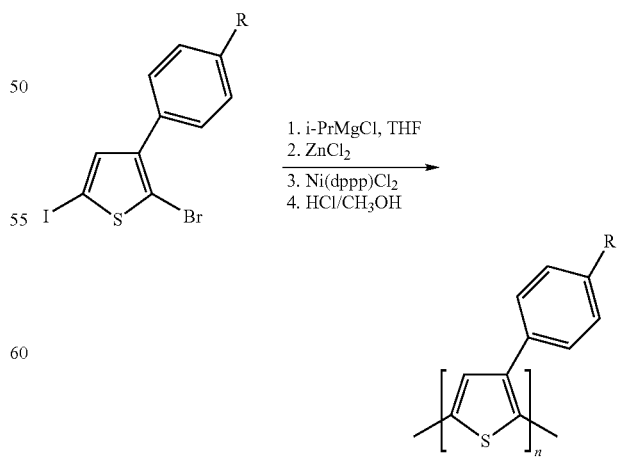

where R is a branched alkyl group, e.g. 2-ethylhexyl.

A dry 100-mL three-neck flask was charged with 2-bromo-3-[4-(2-ethylhexyl)phenyl]-5-iodothiophene (1.43 g, 3 mmol) and flushed with $N_2$, and THF (20 mL) was added via syringe. A 2 M solution of iso-propylmagnesium chloride (1.5 mL, 3 mmol) in THF was added via a deoxygenated syringe and the reaction mixture was stirred at ambient temperature for 10 minutes. Anhydrous $ZnCl_2$ (0.45 g, 3.3 mmol) was added in one portion and completely dissolved after 30 minutes of stirring. A suspension of Ni(dppp)$Cl_2$ (8 mg, 0.014 mmol) in THF (0.01 M) was added via syringe. The reaction mixture was heated to 55° C. and stirred for 12 hours. Hydrochloric acid (5 N) was added and the reaction mixture was precipitated into methanol. The polymer was filtered, washed in sequence with more methanol and hexanes, and dried under vacuum to yield the product as a dark orange solid (60-83%): $M_n$=9,000; $M_w$=12,600; PDI=1.4 (GPC: $CHCl_3$, $\lambda_{max}$=254 nm, 35° C.).

Working Example 4

Polymerization Via the Universal GRIM Method

The following polymer, poly(3-[4-(2-ethylhexyl)-phenyl]thiophene), was prepared via the Universal GRIM method utilizing 2-bromo-3-[4-(2-ethylhexyl)phenyl]-5-iodothiophene:

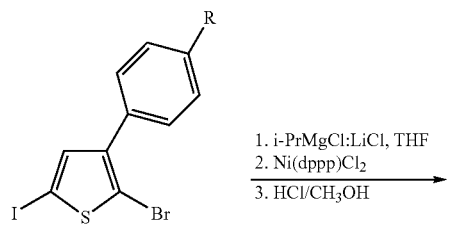

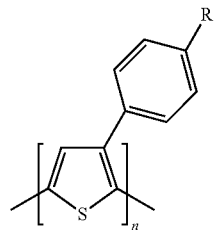

R:ethyl-hexyl where R is a branched alkyl group, e.g. 2-ethylhexyl.

A dry, 100-mL, three-neck flask was charged with 2-bromo-3-[4-(2-ethylhexyl)phenyl]-5-iodothiophene (0.5 g, 1 mmol) and flushed with $N_2$, and THF (10 mL) was added via syringe. A 1-M solution of iso-propylmagnesium chloride:lithium chloride (1 mL, 1 mmol) in THF was added via a deoxygenated syringe and the reaction mixture was stirred at ambient temperature for 10 minutes. A suspension of Ni(dppp)$Cl_2$ (2 mg, 0.003 mmol) in THF (0.003 M) was added via syringe. The reaction mixture was heated to 55° C. and stirred for 2 hours. Hydrochloric acid (5 N) was added and the reaction mixture was precipitated into methanol. The polymer was filtered, washed in sequence with more methanol and hexanes, and dried under vacuum to yield the product as a dark orange solid (60-83%): $M_n$=46,900; $M_w$=57,000; PDI=1.2 (GPC: $CHCl_3$, $\lambda_{max}$=254 nm, 35° C.).

Working Example 5

Synthesis of poly(3-hexylthiophene)-b-poly{3-[4-(2-ethylhexyl)-phenyl]thiophene} Via Chain Extension Polymerization Utilizing the GRIM Method and the Universal GRIM Method The block-copolymer, poly(3-hexylthiophene)-b-poly{3-[4-(2-ethylhexyl)-phenyl]thiophene} (P3HT-PPEHPT), was prepared via a combination of the GRIM and Universal GRIM methodologies utilizing 2-bromo-3-hexyl-5-iodothiophene and 2-bromo-3-[4-(2-ethylhexyl)phenyl]-5-iodothiophene, as shown below.

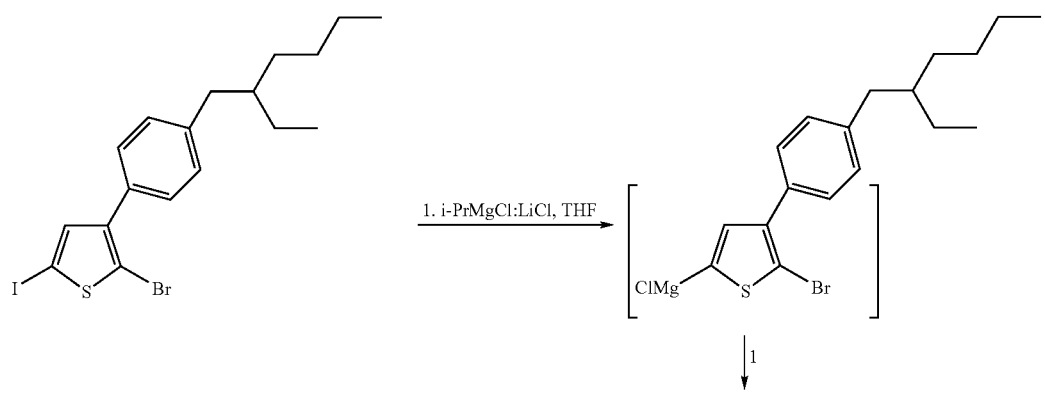

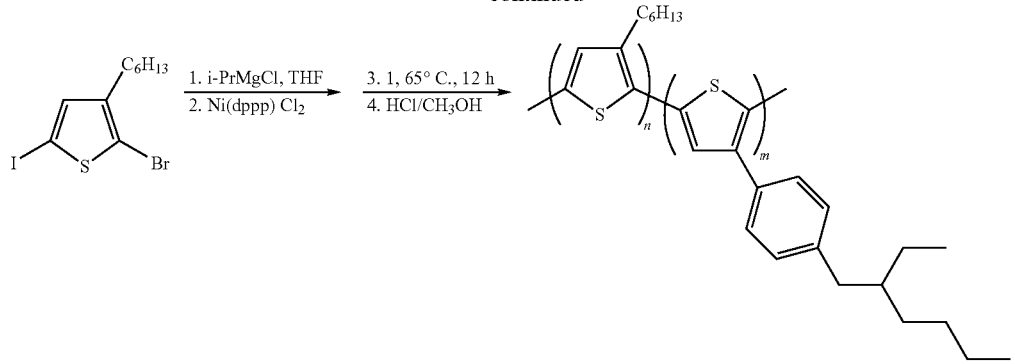

A dry 25-mL three-neck round bottom flask was flashed with $N_2$ and charged with 2-bromo-3-[4-(2-ethylhexyl)phenyl]-5-iodothiophene (0.67 g, 1.4 mmol) and anhydrous THF (5.0 mL) via syringe. A 1 M solution of iso-propylmagnesium chloride:lithium chloride (1.3 mL, 1.4 mmol) in THF was added via a deoxygenated syringe and the reaction mixture (1) was kept stirring at ambient temperature for the next step. Another dry 100-mL three-neck round bottom flask equipped with a condenser was flashed with $N_2$ and charged with 2-bromo-3-hexyl-5-iodothiophene (0.26 g, 0.7 mmol), dodecane (0.1 mL) (internal standard), and anhydrous THF (23 mL) via syringe. A 2 M solution of iso-propylmagnesium chloride (0.34 mL, 0.7 mmol) in THF was added via a deoxygenated syringe and the reaction mixture was stirred at ambient temperature for 10 minutes. A suspension of Ni(dppp)Cl$_2$ (5.2 mg, 9.6×10$^{-6}$ mmol) in THF (0.01 M) was added via syringe. The reaction mixture was heated to 35° C. and stirred for 45 minutes, whereupon the content of the first flask (1) was introduced to the polymerization flask via a deoxygenated syringe. The reaction mixture was heated to 55° C. and stirred for 16 hours. Hydrochloric acid (5 N) was added and the reaction mixture was precipitated into methanol. The polymer was filtered, washed in sequence with more methanol and hexanes, and dried under vacuum to yield the product as a dark purple solid (50%): $M_n$=34,800; $M_w$=85,500; PDI=2.5 (GPC: CHCl$_3$, $\lambda_{max}$=254 nm, 35° C.).

Example 6

General Procedure for Polymerization of Poly(3-[R-aryl]thiophene)s, where R is H, Linear, or Branched Alkyl Group at Para, Ortho or Meta Position, Via the GRIM Method Poly(3-[R-aryl]thiophene)s, where R is H, linear, or branched alkyl group, are synthesized utilizing 2-bromo-(3-[R-aryl]thiophene)-5-iodo-thiophene precursors.

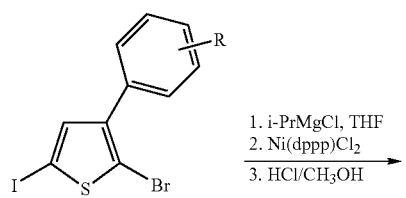

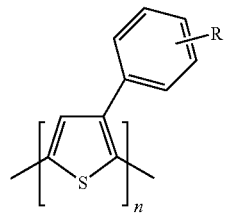

R:H, branced, or linear group

In a typical polymerization experiment, a dry 100-mL three-neck flask equipped with a condenser is charged with 2-bromo-(3-[p-R-aryl]thiophene)-5-iodo-thiophene (1 mmol) and flushed with $N_2$, and THF (10 mL) is added via syringe. A 2 M solution of iso-propylmagnesium chloride (1 mmol) in THF is added via a deoxygenated syringe and the reaction mixture is stirred at ambient temperature for 10 minutes. A suspension of Ni(dppp)Cl$_2$ (0.2-2 mol %) in THF (0.01 M) is added via syringe. The reaction mixture is heated to 55° C. and stirred for 2 to 12 hours. Hydrochloric acid (5 N) is added and the reaction mixture is precipitated into methanol. The polymer is filtered, washed in sequence with more methanol and hexanes, and dried under vacuum. The molecular weight of the polymer is measured by GPC.

Example 7

General Procedure for Polymerization of Poly(3-[R-aryl]thiophene)s, where R is H, Linear, or Branched Alkyl Group at the Para, Ortho or Meta Position, Via the Universal Grim Method Poly(3-[R-aryl]thiophene)s, where R is H, linear or branched alkyl group, are synthesized utilizing 2-bromo-(3-[R-aryl]thiophene)-5-iodo-thiophene precursors.

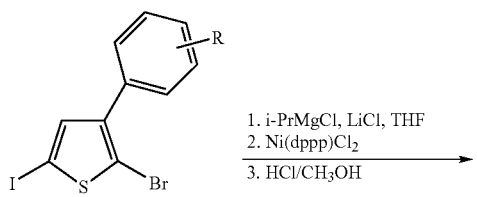

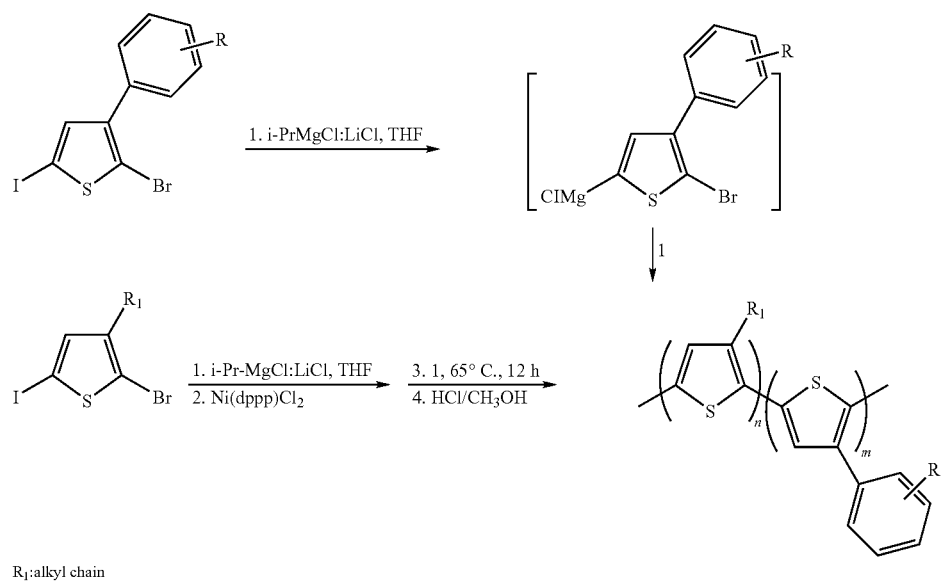

R₁: alkyl chain
R: H, branched/linear alkyl chain

-continued

R: H, branced, or linear group

In a typical polymerization experiment, a dry 100-mL three-neck flask equipped with a condenser is charged with 2-bromo-(3-[p-R-aryl]thiophene)-5-iodo-thiophene (4.2 mmol) and flushed with $N_2$, and THF (42 mL) is added via syringe. A 1 M solution of iso-propylmagnesium chloride:lithium chloride (4.2 mmol) in THF is added via a deoxygenated syringe and the reaction mixture is stirred at ambient temperature for 10 minutes. A suspension of Ni(dppp)Cl₂ (0.2-2 mol %) in THF (0.01 M) is added via syringe. The reaction mixture is heated to 55° C. and stirred for 2 to 12 hours. Hydrochloric acid (5 N) is added and the reaction mixture is precipitated into methanol. The polymer is filtered, washed in sequence with more methanol and hexanes, and dried under vacuum. The molecular weight of the polymer is measured by GPC.

Example 8

General Procedure for Synthesis of 3-Alkyl-Functionalized and 3-[R-aryl]thiophene copolymers, where R is H, Branched, or Linear Alkyl Group at the para, ortho or meta Position, via the Universal GRIM Method Copolymers of poly(3-alkyl-thiophene)-b-poly(3-[R-aryl]thiophene)s, where R is H, branched, or linear alkyl group, $R_1$ is a linear or branched alkyl, are synthesized utilizing 2-bromo-3-alkyl-5-iodothiophenes and 2-bromo-(3-[R-aryl]thiophene)-5-iodo-thiophene precursors.

A dry 25-mL three-neck round bottom flask is flashed with $N_2$ and charged with bromo-(3-[R-aryl]thiophene)-5-iodo-thiophene (1.8 mmol) and anhydrous THF (6.0 mL) via syringe. A 1 M solution of iso-propylmagnesium chloride:lithium chloride (1.8 mmol) in THF is added via a deoxygenated syringe and the reaction mixture (1) is kept stirring at ambient temperature for the next step. Another dry 100-mL three-neck round bottom flask equipped with a condenser is flashed with $N_2$ and charged with 2-bromo-3-alkyl-5-iodothiophene (1.0 mmol), dodecane (0.1 mL) (internal standard), and anhydrous THF (31 mL) via syringe. A 1 M solution of iso-propylmagnesium chloride:lithium chloride (1.0 mmol) in THF is added via a deoxygenated syringe and the reaction mixture is stirred at ambient temperature for 10 minutes. A suspension of Ni(dppp)Cl₂ (0.2-2 mol %) in THF (0.01 M) is added via syringe. The reaction mixture is heated to 35° C. and stirred for 45 minutes, whereupon the content of the first flask (1) is introduced to the polymerization flask via a deoxygenated syringe. The reaction mixture is heated to 55° C. and stirred for 24 hours. Hydrochloric acid (5 N) is added and the reaction mixture is precipitated into methanol. The polymer is filtered, washed in sequence with more methanol and hexanes, and dried under vacuum. The molecular weight of the polymer is measured by GPC.

Working Example 9

Thermochromism Reduction in Aryl-Substituted Polythiophenes, wherein the Aryl Group has a Branched Alkyl Substituent Materials can be prepared by methods described herein which can show reduced thermochromism. See for example U.S. Provisional Patent Application 60/938,166 filed May 15, 2007 to Sheina et al. and FIGS. 1-3, which is incorporated by reference in its entirety.

Working Example 10

Fabrication of an Organic Photovoltaic Cell from a Polymer

The photovoltaic devices comprise patterned indium tin oxide (ITO, anode, 60Ω/square) on glass substrate (Thin Film Devices, Anaheim, Calif.); a thin layer of HIL (30 nm thick) consisting of PEDOT/PSS (Baytron, AI 4083, H C Stark); a 100- to 200-nm layer of PEHPT blended with methanofullerence [6,6]-phenyl C61-butyric acid methyl ester (PCBM) (Nano-C, Westwood, Mass.) (an n-type component); and a Ca/Al bilayer cathode.

The patterned ITO glass substrates were cleaned with detergent, hot water, and organic solvents (acetone and alcohol) in an ultrasonic bath and treated with ozone plasma immediately prior to device layer deposition. The HIL solution was then spin-coated onto the patterned ITO glass substrate to achieve a thickness of 30 nm. The film was annealed at 150° C. for 30 minutes in a nitrogen atmosphere. The active layer was formulated to a 1.2:1 or 1.5:1 weight ratio polymer:n-type blend in chlorobenzene. The formulation was made to 0.024% volume solids and was then spun onto the top of the HIL film, resulting in no damage to the HIL (verified by AFM). The film was then annealed in the range of 175° C. to 200° C. for 30 minutes in a glove box. Next, a 5-nm Ca layer was thermally evaporated onto the active layer through a shadow mask, followed by deposition of a 150-nm Al layer. The devices were then encapsulated via a glass cover slip (blanket). Encapsulation was sealed with EPO-TEK OG112-4 UV curable glue. The encapsulated device was cured under UV irradiation (80 mW/cm$^2$) for 4 minutes and tested as follows.

The photovoltaic characteristics of devices under white light exposure (Air Mass 1.5 Global Filter) were measured using a system equipped with a Keithley 2400 source meter and an Oriel 300W Solar Simulator based on a Xe lamp with output intensity of 100 mW/cm$^2$ (AM1.5G). The light intensity was set using an NREL-certified Si-KG5 silicon photodiode.

The power conversion efficiency of a solar cell is given as $\eta=(FF|J_{sc}|V_{oc})/P_{in}$, where FF is the fill factor, $J_{sc}$ is the current density at short circuit, $V_{oc}$ is the photovoltage at open circuit and $P_{in}$ is the incident light power density. The $J_{sc}$, $V_{oc}$ and efficiency ($\eta$%) measured for each OPV device (e.g., a standard OPV device with an ITO/PEDOT:PSS/Active Layer/Ca/Al configuration, where Active Layer is comprised of a p/n composite deposited from a single solvent system) are shown in Table 1, below, compared to the control device which was made as described above using poly(3-hexylthiophene) as the p-type and PCBM as the n-type materials. The data clearly show a significant improvement in the $V_{oc}$ for the OPV cell made with EPHT or P3HT-PPEHPT, compared to the OPV cell made with P3HT.

TABLE 1

| p-type polymer | Mn (PDI)[1] | n-type component | p/n ratio | Solvent[2] | $J_{SC}$ (mA/cm$^2$) | $V_{OC}$ (V) | FF | $\eta$(%) | Method of Synthesis[3] |
|---|---|---|---|---|---|---|---|---|---|
| P3HT | 52,500 (1.5) | PCBM | 1.2:1 | DCB | 10.02 | 0.58 | 0.65 | 3.75 | GRIM (Br/Br) |
| PEHPT | 15,600 (2.8) | PCBM | 1.5:1 | CB | 4.18 | 0.78 | 0.45 | 1.47 | McCullough (Br) |
| PEHPT | 15,600 (2.8) | Indene mono-C60 | 1.2:1 | CB | 4.83 | 0.86 | 0.57 | 2.44 | McCullough (Br) |
| PEHPT | 15,600 (2.8) | Indene bis-C60 | 1.2:1 | CB | 3.32 | 1.02 | 0.52 | 1.77 | McCullough (Br) |
| PEHPT | 9,300 (1.2) | PCBM | 1.2:1 | CB | 3.19 | 0.72 | 0.41 | 0.94 | GRIM |
| PEHPT | 19,500 (1.3) | PCBM | 1.2:1 | CB | 4.37 | 0.69 | 0.65 | 1.96 | Universal GRIM (I/Br) |
| PEHPT | 43,000 (1.3) | PCBM | 1.2:1 | CB | 5.29 | 0.70 | 0.58 | 2.12 | Universal GRIM (I/Br) |
| P3HT-PPEHPT | 25,000 (1.8) | PCBM | 1.2:1 | CB | 8.23 | 0.62 | 0.66 | 3.34 | GRIM (I/Br) |
| P3HT-PPEHPT | 25,000 (1.8) | Indene bis-C60 | 1.2:1 | CB | 4.89 | 0.89 | 0.52 | 2.28 | GRIM (I/Br) |
| P3HT-PPEHPT | 25,000 (1.8) | Indene tris-C60 | 1.2:1 | CB | 2.05 | 1.01 | 0.41 | 0.84 | GRIM (I/Br) |

[1]Number average molecular weight and polydispersity index ($M_n$ and PDI, respectively) were determined via Gel Permeation Chromatography (GPC) with chloroform as the eluent (flow rate 1.0 mL/min, 35° C., λ = 254 nm) against polystyrene standards with toluene used as an internal standard
[2]Solvent: dichlorobenzene (DCB); chlorobenzene (CB)
[3]A series of regioregular 3-alkyl/aryl-functionalized polythiophenes were synthesized via either the GRIM route [a) Lowe, R. S.; McCullough, R. D. Adv. Mater. 1999, 11, 250; b) Iovu, M. C., Sheina, E. E., Gil, R. R., McCullough, R. D. Macromolecules 2005, 38, 8649], the McCullough methodology [a) McCullough, R. D.; Williams, S. P.; Tristram-Nagle, S.; Jayaraman, M.; Ewbank, P. C.; Miller, L. Synth. Met. 1995, 67, 279; b) Sheina, E. E., Liu, J., Iovu, M. C., Laird, D. W., McCullough, R. D. Macromolecules 2004, 37, 3526], or the Universal GRIM [Iovu., M. C.; McCullough, R. D. et al. Patent application filed, 60/841,548 filed Sep. 1, 2006, and U.S. Regular Patent Application No. 11/849,229, filed on Aug. 31, 2007 to McCullough et al, its corresponding PCT/US2007/077461 published as WO2008/028166] utilizing dibrominated (Br/Br), monobrominated (Br), and iodo-brominated (I/Br) monomer precursors, respectively.

Working Example 11

Thermal Stability of Organic Photovoltaic Cells Incorporating Aryl-Substituted Polythiophenes, wherein the Aryl Group has a Branched Alkyl Substituent OPV cells having the same device configuration as described above were fabricated using the procedure described in Example 10. The OPV cells were fabricated with active layers of either POPT or PEHPT as the p-type component with PCBM as the n-type component and chlorobenzene as a solvent. The active layers of the devices had different p/n ratios and were annealed at different temperatures, as indicated in Table 2. The p-type components for the active layers were synthesized using either the GRIM or the McCullough method.

TABLE 2

| p-type polymer[1] | n-type component | p/n ratio | Solvent[2] | Annealing T° C. (min) | $J_{SC}$ mA/cm$^2$ | $V_{OC}$ V | FF | η % | Method of Synthesis[3] |
|---|---|---|---|---|---|---|---|---|---|
| POPT | PCBM | 1.2:1 | CB | 110 (30) | 2.7 | 0.57 | 0.33 | 0.52 | GRIM |
| POPT | PCBM | 1.2~1 | CB | 175 (30) | 0.18 | 0.40 | 0.32 | 0.02 | GRIM |
| POPT | PCBM | 1.5~1 | CB | 70 (30) | 1.39 | 0.66 | 0.33 | 0.3 | GRIM |
| POPT | PCBM | 1.5~1 | CB | 135 (30) | 2.31 | 0.55 | 0.32 | 0.41 | GRIM |
| POPT | PCBM | 1.5:1 | CB | 175 (30) | 0.39 | 0.47 | 0.3 | 0.05 | GRIM |
| PEHPT | PCBM | 1.2~1 | CB | 175 (30) | 3.19 | 0.72 | 0.41 | 0.94 | GRIM |
| PEHPT | PCBM | 1.2~1 | CB | 175 (30) | 4.66 | 0.79 | 0.48 | 1.76 | McCullough |
| PEHPT | PCBM | 1.2~1 | CB | 200 (30) | 4.26 | 0.75 | 0.45 | 1.46 | McCullough |
| PEHPT | PCBM | 1.2~1 | CB | 200 (10) | 4.66 | 0.78 | 0.47 | 1.71 | McCullough |

[1] GRIM-POPT [$M_n$ = 17,000 (PDI = 3.4)]; GRIM-PEHPT [$M_n$ = 9,300 (PDI = 1.2)]; McCullough-PEHPT [$M_n$ = 15,600 (PDI = 2.8)]
[2] Solvent: chlorobenzene (CB)
[3] A series of regioregular 3-alkyl/aryl-functionalized polythiophenes were synthesized via either the GRIM route [a) Lowe, R. S.; Khersonsky, S. M.; McCullough, R. D. Adv. Mater. 1999, 11, 250; b) Iovu, M. C., Sheina, E. E., Gil, R. R., McCullough, R. D. Macromolecules 2005, 38, 8649] or the McCullough methodology [a) McCullough, R. D.; Williams, S. P.; Tristram-Nagle, S.; Jayaraman, M.; Ewbank, P. C.; Miller, L. Synth. Met. 1995, 67, 279; b) Sheina, E. E., Liu, J., Iovu, M. C., Laird, D. W., McCullough, R. D. Macromolecules 2004, 37, 3526]. Number and weight average molecular weights ($M_n$ and $M_w$, respectively) were determined via Gel Permeation Chromatography (GPC) with chloroform as the eluent (flow rate 1.0 mL/min, 35° C., λ = 254 nm) against polystyrene standards with toluene used as an internal standard.

The superior thermal stability of PEHPT relative to POPT is evident from the OPV device data. It can be seen from the results in Table 2 that high temperatures were detrimental to the device performance where active layer was comprised of POPT whereas OPV cells incorporating PEHPT exhibited relatively high efficiencies (e.g., η% ≧ 1, ≧ 1.4, or even ≧ 1.7) even after being annealed at 200° C.

Working Example 12

Methods for the Production of POPT

In addition to improved aryl-substituted conjugated polymers, improved methods for producing POPT are provided. Specifically, it has been discovered that the properties of POPT can be improved when POPT is produced using a GRIM, modified GRIM, McCullough, or modified McCullough methods. This Example and Example 14, below, illustrate improved methods for producing POPT and methods for making copolymers thereof.

The following block-copolymer, poly[(3-butylthiophene)-b-(3-(4-octylphenyl)thiophene], was prepared via a combination of the modified GRIM and McCullough methodologies:

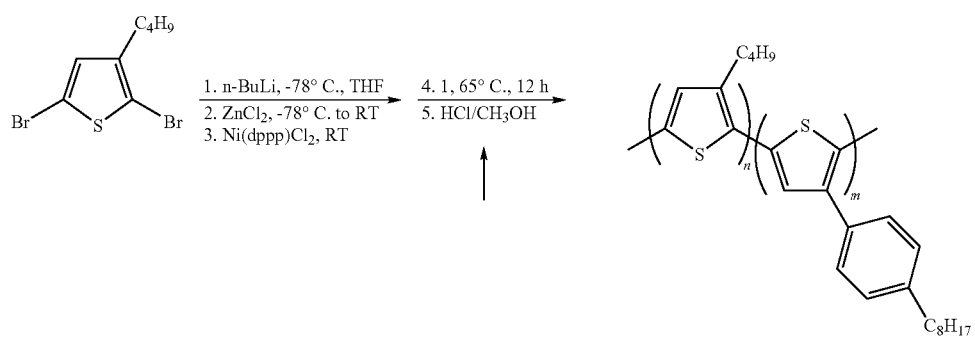

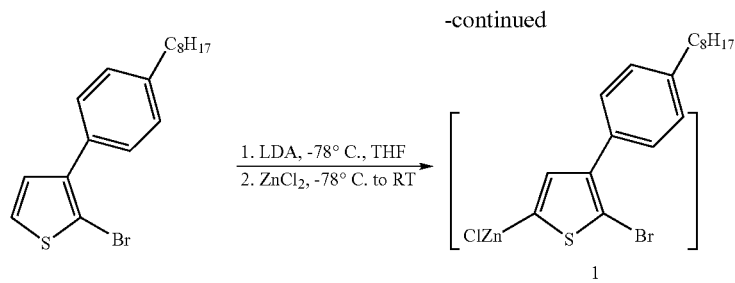

A dry 25-mL three-neck round bottom flask was flashed with $N_2$ and charged with 2-bromo-3-(4-octylphenyl)thiophene (1.2 g, 3.5 mmol) and anhydrous THF (4 mL) via syringe. The reaction flask is chilled to −76° C. for the next step.

A dry 25-mL three-neck flask was flushed with $N_2$ and charged with diisopropylamine (0.57 mL, 4.1 mmol) and anhydrous THF (8 mL), in which both were added via syringe. The reaction flask was cooled to 0° C. and n-butyllithium (1.7 mL, 3.5 mmol) was added dropwise via syringe. After 20 minutes of stirring at 0° C., the solution was chilled to −76° C. (acetone/dry ice bath) and stirring continued for 5 minutes. To this reaction mixture a previously-chilled-to −76° C. 1 M THF solution of 2-bromo-3-(4-octylphenyl)thiophene was added via cannula. The reaction mixture was stirred for 1 hour at −76° C. Anhydrous $ZnCl_2$ (0.50 g, 3.6 mmol) was added in one portion and completely dissolved after 30 minutes of stirring. The cooling bath was removed and the reaction mixture (1) was allowed to warm to ambient temperature and was kept at ambient temperature for the next step.

for 10 minutes. Anhydrous $ZnCl_2$ (0.25 g, 1.87 mmol) was added in one portion and completely dissolved after 30 minutes of stirring. A suspension of Ni(dppe)$Cl_2$ (5.3 mg, 0.010 mmol) in 1 mL of THF was added via syringe. The reaction mixture was stirred at ambient temperature for 10 minutes, at which point 1 was transferred to this 100-mL three-neck round bottom flask. The reaction mixture was heated to 65° C. and stirred for 12 hours. Hydrochloric acid (5 N) was added and the reaction mixture is precipitated into methanol. The polymer was filtered, washed in sequence with more methanol and hexanes, and dried under vacuum to yield the product as a dark orange solid (60-83%): $M_n$=11,000; $M_w$=17,600; PDI=1.6 (GPC: $CHCl_3$, $\lambda_{max}$=254 nm, 35° C.).

Working Example 13

General Procedure for Preparation of Block Copolymers of Alkyl-Substituted and Phenyl-Substituted Polythiophenes Via a Combination of the GRIM and the Universal GRIM Methodologies

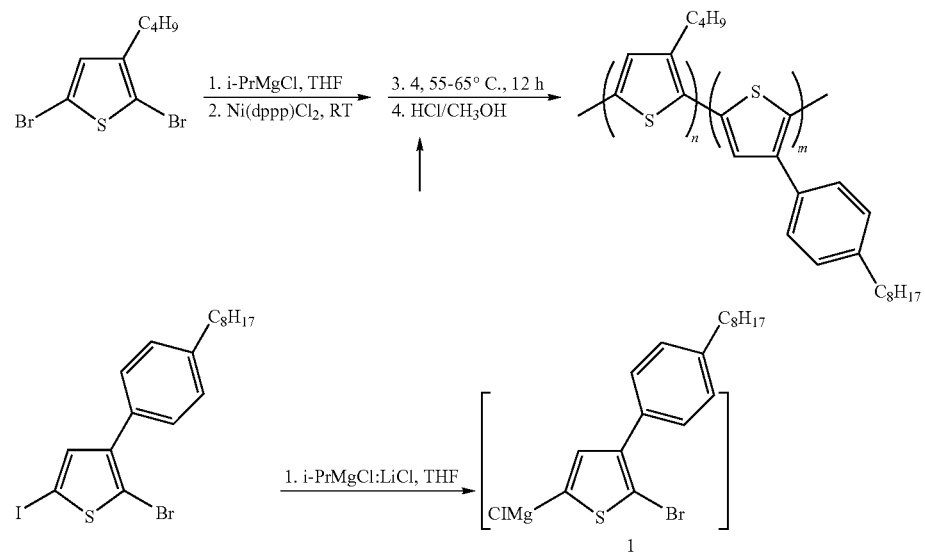

Another 100-mL three-neck round bottom flask was flushed with $N_2$ and charged with 2,5-dibromo-3-butylthiophene (0.5 g, 1.7 mmol) and anhydrous THF (55 mL). A 2 M solution of n-butyllithium (0.85 mL, 1.7 mmol) was added via a deoxygenated syringe. The reaction mixture was stirred A dry 25-mL three-neck round bottom flask was flashed with $N_2$ and charged with 2-bromo-5-iodo-3-(4-octylphenyl)thiophene (1.7 g, 3.5 mmol) and anhydrous THF (12 mL) via syringe. A 1 M solution of iso-propylmagnesium chloride: lithium chloride (3.5 mL, 3.5 mmol) in THF was added via a deoxygenated syringe. The reaction mixture was stirred for 10 minutes at ambient temperature and the conversion of the monomer to the Grignard reagent was monitored by GC-MS analysis. The reaction flask (1) was kept at ambient temperature for the next step.

Another dry 100-mL three-neck round bottom flask was flushed with $N_2$ and charged with 2,5-dibromo-3-butylthiophene (0.5 g, 1.7 mmol) and anhydrous THF (55 mL). A 2 M solution of iso-propylmagnesium chloride (0.85 mL, 1.7 mmol) in THF was added via a deoxygenated syringe. The reaction mixture was stirred for 10 minutes. The conversion of 2,5-dibromo-3-butyllthiophene to 2-bromo-5-chloromagnesium-3-butylthiophene was monitored by the GC-MS analysis. At complete conversion, a suspension of Ni(dppe)$Cl_2$ (5.3 mg, 0.01 mmol) in 1 mL of anhydrous THF was added to the reaction flask via a deoxygenated syringe. The reaction mixture was stirred at ambient temperature for 10 minutes, at which point 1 was transferred to this 100-mL three-neck round bottom flask. The reaction mixture was heated to 65° C. and stirred for 12 hours. Hydrochloric acid (5 N) was added and the reaction mixture was precipitated into methanol. The polymer was filtered, washed in sequence with more methanol and hexanes, and dried under vacuum. The molecular weight of the polymer was measured by GPC.

Table 3 below provides a summary of material characteristics for the poly[3-(4-octylphenyl)thiophene] films produced as described in Examples 13 and 14 as a function of the method of synthesizing POPT. Also shown is the effect on the $V_{OC}$ of an OPV cell having a POPT active layer, wherein the POPT layer is made using different methods of synthesis. For comparison, the results for a POPT film made using the well-known $FeCl_3$ method are also shown.

TABLE 3

| p-Type polymer | Mw | PDI | HOMO eV | $\lambda_{max}$ nm | $Eg^{UV}$ eV | $V_{OC}$ V | Method of Synthesis |
|---|---|---|---|---|---|---|---|
| POPT | 44,300 | 1.6 | −5.22 | 558 | 1.77 | ~0.5 | $FeCl_3$ |
| POPT | 49,100 | 1.6 | −5.28 | 542 | 1.80 | ~0.6-0.7 | GRIM |
| POPT | 36,400 | 1.4 | −5.37 | 561 | 1.7 | ~0.45 | McCullough |
| POPT | 46,730 | 1.8 | −5.38 | 554 | 1.8 | ~0.6 | McCullough |

Example 14

Fabrication of OFET and OPV from a Polymer of the Present Invention

Polymers have been utilized in OFETs and OPV devices. Several polymers of alkyl-substituted and aryl-substituted thiophenes were synthesized via the GRIM, Universal GRIM, or McCullough method utilizing either organic Br—Br or Br—I dihalide derivatives. The data are provided below in Tables 4 and 5 for OPV and OFET devices, respectively.

TABLE 4

Summary of photovoltaic characterization data for organic solar cells[1] illustrating a strong dependence of the solar cell performance on the structural purity of p-type.

| p-type polymer[2] | n-type component | p/n ratio | Solvent[3] | $J_{SC}$ (mA/cm$^2$) | $V_{OC}$ (V) | FF | η(%) | Method of Synthesis[4] |
|---|---|---|---|---|---|---|---|---|
| P3HT | PCBM | 1.2:1 | xylene | 6.49 | 0.64 | 0.40 | 1.67 | GRIM (Br/Br) |
| P3HT | PCBM | 1.2:1 | xylene | 7.54 | 0.61 | 0.61 | 2.82 | GRIM (Br/I) |
| PEHPT | Indene mono-C60 | 1.2:1 | CB | 3.95 | 0.85 | 0.45 | 1.55 | McCullough (Br) |
| PEHPT | Indene mono-C60 | 1.2:1 | CB | 4.59 | 0.74 | 0.53 | 1.84 | UGRIM (Br/I) |
| PEHPT | PCBM | 1.2:1 | CB | 6.60 | 0.70 | 0.56 | 2.60 | UGRIM (Br/I) |

[1]Solar cells were fabricated with a ITO/PEDOT:PSS/Active Layer/Ca/Al configuration, where Active Layer is comprised of a p/n composite deposited from a single solvent system

[2]Polymers: P3HT—poly(3-hexylthiophene); PEHPT—poly(3-[4-(2-ethylhexyl)-phenyl]thiophene)

[3]Solvent: chlorobenzene (CB)

[4]A series of regioregular 3-alkyl/aryl-functionalized polythiophenes were synthesized via either the GRIM route [a) Lowe, R. S.; Khersonsky, S. M.; McCullough, R. D. Adv. Mater. 1999, 11, 250; b) Iovu, M. C., Sheina, E. E., Gil, R. R., McCullough, R. D. Macromolecules 2005, 38, 8649], the McCullough methodology [a) McCullough, R. D.; Williams, S. P.; Tristram-Nagle, S.; Jayaraman, M.; Ewbank, P. C.; Miller, L. Synth. Met. 1995, 67, 279; b) Sheina, E. E., Liu, J., Iovu, M. C., Laird, D. W., McCullough, R. D. Macromolecules 2004, 37, 3526], or the Universal GRIM [Iovu., M. C.; McCullough, R. D. et al. Patent application filed, 60/841,548 filed Sep. 1, 2006, and U.S. Regular Patent Application No. 11/849,229, filed on Aug. 31, 2007 to McCullough et al, its corresponding PCT/US2007/077461 published as WO2008/028166,] utilizing dibrominated (Br/Br), monobrominated (Br), and iodo-brominated (I/Br) monomer precursors, respectively.

TABLE 5

Summary of OFET[1] characterization data illustrating a strong dependence of the OFET mobility on the structural purity of a conjugated polymer.

| p-type polymer[2] | μ (cm²/Vs) | $I_{ON}$ (μA) | Method of Synthesis[3] |
|---|---|---|---|
| P3HT | $5.64 \times 10^{-4}$ | 13.9 | GRIM (Br/Br) |
| P3HT | $7.44 \times 10^{-3}$ | 283 | GRIM (Br/I) |
| PEHPT | $3.43 \times 10^{-4}$ | 6.32 | McCullough (Br) |
| PEHPT | $1.08 \times 10^{-3}$ | 16.0 | UGRIM (Br/I) |

[1]Organic field effect transistors (OFETs) were fabricated with a bottom gate configuration, where Active Layer is comprised of a p-type deposited from a single solvent system (see below). See also "OFET Device Fabrication" section below.
[2]Polymers: P3HT—poly(3-hexylthiophene); PEHPT—poly(3-[4-(2-ethylhexyl)-phenyl] thiophene)
[3]A series of regioregular 3-alkyl/aryl-functionalized polythiophenes were synthesized via either the GRIM route [a) Lowe, R. S.; Khersonsky, S. M.; McCullough, R. D. Adv. Mater. 1999, 11, 250; b) Iovu, M. C., Sheina, E. E., Gil, R. R., McCullough, R. D. Macromolecules 2005, 38, 8649], the McCullough methodology [a) McCullough, R. D.; Williams, S. P.; Tristram-Nagle, S.; Jayaraman, M.; Ewbank, P. C.; Miller, L. Synth. Met. 1995, 67, 279; b) Sheina, E. E., Liu, J., Iovu, M. C., Laird, D. W., McCullough, R. D. Macromolecules 2004, 37, 3526], or the Universal GRIM [Iovu., M. C.; McCullough, R. D. et al. Patent application filed, 60/841,548 filed Sep. 1, 2006, and U.S. Regular Patent Application No. 11/849,229, filed on Aug. 31, 2007 to McCullough et al, its corresponding PCT/US2007/077461 published as WO2008/028166] utilizing dibrominated (Br/Br), monobrominated (Br), and iodo-bromominated (I/Br) monomer precursors, respectively.

OFET Device Fabrication

Organic transistors were fabricated on a highly doped n-type Si wafer with 250 nm thermally grown $SiO_2$ as the gate dielectric layer. Interdigitized Drain and Source Ti/Au electrodes were fabricated using conventional "lift-off" photolithography followed by sputtering of 50 nm Au over 3 nm titanium. The channel length and width are 10 μm and 10 mm, respectively. In order to statistically analyze data, the multiple devices with the same channel dimensions were designed and fabricated on a single square Si substrate. Before applying the polymer film, the surface of the $SiO_2$/Si substrates was treated with either spun-cast hexamethylenedisilazane (HMDS) thin layer or a self-assembled octyltrichlorosilane (OTS-8) monolayer. Organic semiconducting layers were deposited by spin-coating from o-dichlorobenzene at a concentration of 10 mg/ml. Prior to deposition, the solutions were put on a shaker at 40° C. for 12 hours. The thickness of films on the PFET was about 50 nm determined by KLA Tencor Alpha-Step IQ® Surface Profiler. The electrical characteristics of single PFETs were measured on an Agilent 4155C semiconductor parameter analyzer connected to a probe station with tri-axial cables. For statistical analysis, an automated measurement system comprised of a 52-pin socket, Keithley 2612 source meter and 7011S switch was used. All testing was done in a glove box filled with dry $N_2$.

What is claimed is:

1. A method of making poly(3-arylsubstituted) thiophene, comprising:
providing at least one monomer represented by:

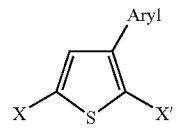

wherein X is I and X' is Br, or X is I and X' is Cl, or X is Br and X' is Cl; and
polymerizing the monomer; and
wherein the aryl group is a substituted phenyl group comprising a branched alkyl substituent.

2. The method of claim 1, wherein X is I, and X' is Br.

3. The method of claim 1, wherein the aryl group is 4-octylphenyl group or 4-(2-ethylhexyl)phenyl group.

4. The method of claim 1, wherein the polymerizing step comprises (i) reacting the monomer with an organomagnesium reagent to form an intermediate, and (ii) reacting the intermediate with at least one metal complex.

5. The method of claim 1, wherein the polymerizing step comprises (i) reacting the monomer with an organomagnesium reagent comprising an organomagnesium component and a metal activation agent to form an intermediate, and (ii) reacting the intermediate with at least one metal complex.

6. The method of claim 1, wherein the polymerizing step comprises dissolving the monomer in at least one solvent to form a mixture, adding at least one organomagnesium reagent to the mixture, adding an initiator to the mixture, recovering a poly(3-arylsubstituted thiophene).

7. The method of claim 1, wherein the polymerizing step is carried out under substantially living conditions.

8. The method of claim 1, wherein the polymerizing is carried out to produce a homopolymer.

9. The method of claim 1, wherein X is I and X' is Br, and wherein the aryl group is an optionally substituted phenyl group, and wherein the polymerizing step comprises (i) reacting the monomer with an organomagnesium reagent to form an intermediate, and (ii) reacting the intermediate with at least one metal complex.

10. A method comprising:
providing an unsaturated ring compound comprising at least two halogen ring substituents, wherein a first halogen ring substituent is iodo and a second halogen ring substituent is bromo,
providing an organomagnesium reagent comprising an organomagnesium component and a metal activation agent,
combining the unsaturated ring compound with the reagent to form a second compound by metal-halogen exchange, wherein the metal activation agent activates the metal halogen exchange,
exposing the second compound to at least one transition metal initiator to produce an oligomerization or polymerization reaction;
wherein the unsaturated ring compound is a thiophene compound substituted at the 3-position with a substituted phenyl group comprising a branched alkyl substitutent.

11. The method of claim 10, wherein the thiophene compound is substituted at the 2-position with bromo and substituted at the 5-position with iodo group.

12. The method of claim 10, wherein the metal activation agent comprises lithium, magnesium, potassium, or zinc.

13. The method of claim 10, wherein the metal activation agent comprises lithium.

14. A method comprising:
providing at least one asymmetrical organic dihalogen polymerization monomer adapted for metal-assisted cross coupling polymerization, wherein the monomer comprises at least one thiophene ring which is substituted with an aryl group, and wherein the monomer comprises an X halogen group and an X' halogen group, wherein X and X' are different and independently Cl, Br, or I,
polymerizing the monomer;
wherein the thiophene ring is substituted at the 3-position with a substituted phenyl group comprising a branched alkyl substitutent.

15. The method of claim 14, wherein the polymerizing step comprises (i) reacting the monomer with an organomagnesium reagent comprising an organomagnesium component and a metal activation agent to form an intermediate, and (ii) reacting the intermediate with at least one metal complex.

16. The method of claim 14, wherein the polymerizing step is carried out under substantially living conditions.

* * * * *